Figure 1:
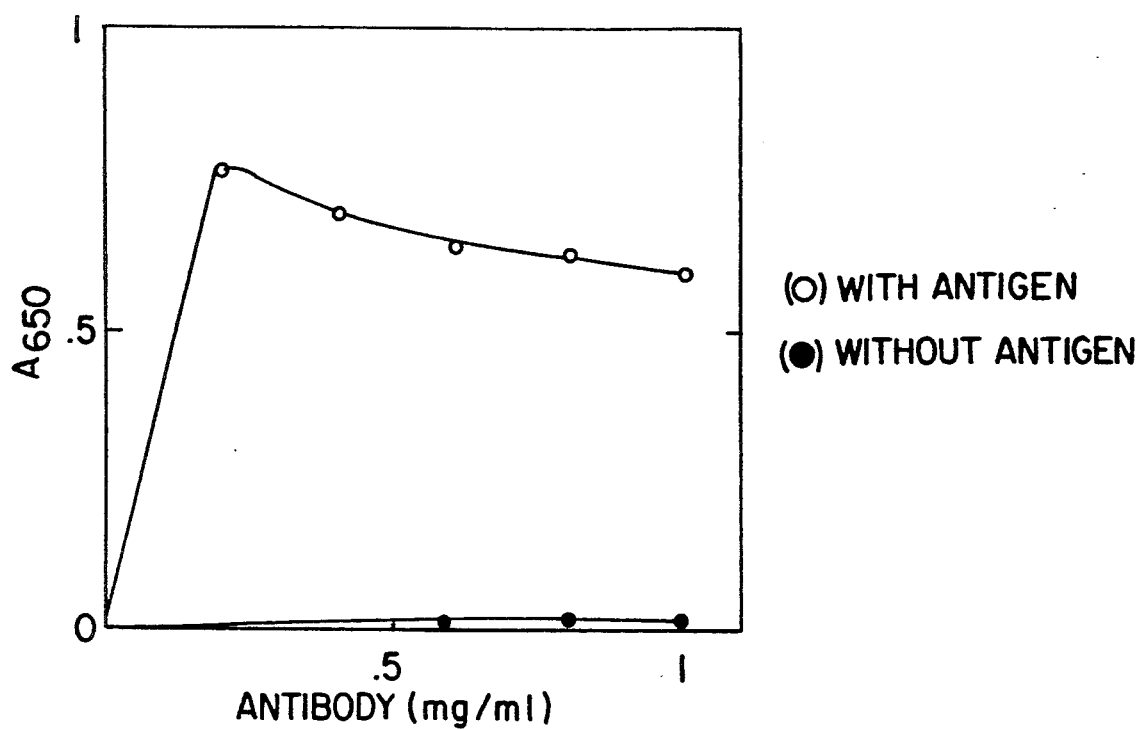

United States Patent [19]

Yamazaki et al.

[11] Patent Number: 5,122,452
[45] Date of Patent: Jun. 16, 1992

[54] ENZYME IMMUNOASSAY WITH A MACROPOROUS HYDROPHOBIC SYNTHETIC POLYMER CLOTH CONTAINING AN IMMOBILIZED ANTIBODY OR ANTIGEN

[75] Inventors: Hiroshi Yamazaki, Nepean; Burton W. Blais, Ottawa, both of Canada

[73] Assignee: Carleton University, Ottawa, Canada

[21] Appl. No.: 652,938

[22] Filed: Feb. 8, 1991

Related U.S. Application Data

[63] Continuation-in-part of Ser. No. 99,393, Sep. 21, 1987, abandoned.

[30] Foreign Application Priority Data

May 20, 1987 [CA] Canada .................................. 537521

[51] Int. Cl.$^5$ ................ G01M 33/535; G01M 33/545; G12N 11/08
[52] U.S. Cl. .................................... 435/7.92; 435/7.9; 435/7.93; 435/174; 435/180; 435/970; 436/528; 436/531
[58] Field of Search .................... 435/7.9, 7.92, 7.93, 435/174, 177, 179, 180, 970; 436/528, 531

[56] References Cited

U.S. PATENT DOCUMENTS

| | | | |
|---|---|---|---|
| 4,200,690 | 4/1980 | Root et al. | 435/174 |
| 4,617,326 | 10/1986 | Bjornberg et al. | 523/111 |
| 4,808,530 | 2/1989 | Means et al. | 435/180 |

OTHER PUBLICATIONS

Morris et al., Immunoassays in Food Analysis, Elsevier Applied Science Publishers, N.Y., 1985, pp. 53-71.
Yamazaki, et al., Biotechnology letters, vol. 8, No. 2, 1984, pp. 107-110.

*Primary Examiner*—David M. Naff
*Attorney, Agent, or Firm*—Harry M. Weiss

[57] ABSTRACT

An immunoassay device containing an immobilized antibody or antigen is provided by directly absorbing and absorbing an unmodified antibody or antigen on and within a woven or non-woven macroporous hydrophobic synthetic polymer cloth formed of a synthetic polymer selected from the group consisting of plypropylene, polyester, nylon and polyethylene. The cloth has a thickness of more than about 200 μm and contains pores in the form of spaces between fibers exceeding about 20 μm in diameter, and has a Frazier Air Permeability in CFM/ft$^2$ at 0.5" H$_2$O of about 215 for a cloth of thickness of about 40 mils. The cloth has a large surface area for binding to an antibody or antigen and can accommodate a large volume of liquid per surface area and has minimum flow resistance. The cloth containing an immobilized antibody or antigen may be used to carry out an enzyme immunoassay by contacting the cloth with a sample containing an antigen or antibody, incubating the cloth with an enzyme-antibody conjugate and then reacting enzyme bound to the cloth with a chromogenic substrate-indicator to produce a visible color. Other immunoassay embodiments may also be carried out and a control cloth can be used such that a difference in color from that obtained with the control cloth determines the amount of antigen or antibody present in a sample.

11 Claims, 2 Drawing Sheets

ENZYME IMMUNOASSAY WITH A MACROPOROUS HYDROPHOBIC SYNTHETIC POLYMER CLOTH CONTAINING AN IMMOBILIZED ANTIBODY OR ANTIGEN

BACKGROUND OF THE INVENTION (i) Related Invention

This invention is a continuation-in-part of co-pending application Ser. No. 099,393 filed Sept. 21, 1987, now abandonedthe entire contents of which are incorporated herein by reference.

(ii) Field of the Invention

This invention relates to the detection of antigens or haptens based on immunoassay techniques.

An antigen is an extraneous substance which, when introduced into the body of vertebrates, causes the production of an antibody which can specifically complex with that antigen. Any substance, for example a protein, which is not normally present in certain organisms, can cause the formation of antibodies when it infiltrates into or is applied to an organism under suitable conditions. An antibody once produced is also capable of binding a hapten, i.e., a relatively small and simple compound which may be the determinant group of a given antigen. The hapten is capable of binding with the specific antibody but is incapable itself of giving rise to the production of an antibody, unless it is bound to an antigenic carrier. These small molecular weight antigens (haptens) may require conjugation with large molecular weight carriers in order to elicit antibody production. This antigen-antibody complexing is the basis of immunoassays.

The binding interaction between an antigen or a hapten and its antibody is specific and sensitive. Other types of materials that participate in similar specific and sensitive binding interactions are: enzymes and their substrates; hormones; vitamins; metabolites; and pharmacological agents; and their receptors and binding substances.

Since virtually any foreign compound can be made immunogenic, the domain of immunoassays is unlimited.

(iii) Description of the Prior Art

Diagnostic tests claim a large share of the health care market. In both human and veterinary medicine, the definitive diagnosis of infectious diseases require the demonstration of the infectious agents or their components. Traditional cultural methods for the detection of pathogens are slow, expensive and of uncertain sensitivity, and require extensive laboratory facilities. To overcome some of these disadvantages, specific binding assay techniques have provided analytical methods for determining various organic substances of diagnostic, medical, environmental and industrial importance which appear in liquid mediums at very low concentrations. Specific binding assays are based on the specific interaction between the ligand, i.e. the bindable analyte under determination, and a binding partner therefor. When one of the ligand and its binding partner is an antibody and the other is a corresponding hapten or antigen, the assay is known as an immunoassay. In addition several immunological tests are now commercially available, namely: agglutination tests; immunofluorescent tests; and enzyme immunoassays. However, many of these tests require the use of microscopes, spectrophotometers, or other laboratory facilities, limiting their use under field conditions. Prompt and effective control of diseases depends on rapid and simple field tests.

Radioimmunoassay employs a radioactive isotope as the label. Such an assay necessarily must follow the heterogeneous format since the monitoraole character of the label is qualitatively unchanged in the free- and bound-species. Because of the inconvenience and difficulty of handling radioactive materials and the necessity of a separation step, homogeneous assay systems have been devised using materials other than radioisotopes as the label component, including enzymes, bacteriophages, metals and organometallic complexes, coenzymes, enzyme substrates, enzyme activators and inhibitors, cycling reactants, organic and inorganic catalysts, prosthetic groups, chemiluminescent reactants, and fluorescent molecules. Such homogeneous specific binding assay systems provide a detectable response, e.g., an electromagnetic radiation signal, e.g. chemiluminescence, fluorescence emission, or color change, related to the presence of amount of the ligand under assay in the liquid sample.

Immunoassays diagnose infectious diseases by detecting either increased titers of antibodies against pathogen antigens or the presence of the pathogens or their antigens. Antigen assays offer more definitive diagnosis of infectious diseases as the capacity to produce antibodies remains in subjects which have recovered from the disease or have previously been vaccinated.

Enzyme immunoassays use enzyme-labeled immunoreagents (antibodies or antigens) for the detection of captured antigens or antibodies captured in a solid phase.

Adsorption onto an easily recoverable solid phase is a simple and rapid means of immobilization of immunoreactants for the subsequent capture of antigens or antibodies from a test sample. Since antibodies and many antigens contain hydrophobic regions in their structures, they bind readily to hydrophobic surfaces. Most commonly used enzyme immunoassays depend on the adsorption of immunoreactants onto either a flat surface or membrane. Solid phases, e.g. microtiter plates, tubes or beads, and plastics, e.g. polystyrene, polyvinyl chloride, nylon, and polymethacrylate have commonly been used. Although nitrocellulose membranes have been used to adsorb antigens as well as antibodies, these are thin and can only accommodate a small volume of test sample which has a limited contact with a surface area. Furthermore, since their pore sizes are small, their effective washing requires a vacuum suction apparatus which holds them airtight.

The patent literature is replete with descriptions of techniques and means for effecting immunoassays. A representative selection of such patents include the following:

1) Canadian Patent 1,031,257 issued May 16, 1978 to R. Dietrich for "Carrier for Immunological Determinations" (directed to a device comprising an immunologically-reactive material on an object carrier or a film, the immunologically-reactive material being in a lyophilised and self-adhering form);

2) Canadian Patent No. 1,060,342 issued Aug. 14, 1979 to O. Lostia et al for "Fibres Incorporating Antibodies, Antigens and Antisera, Method For Their Preparation and Their Use" (directed to a polymeric structure comprising a porous artificial fibre where the substance occluded in the fibre was antibodies, antigens or antisera, and where the pores of the fibre were of such nature as to prevent escape of the occluded substance but to allow for the penetration of the agent that is to be reacted with that substance);

3) Canadian Patent No. 1,083,036 issued Aug. 5, 1980 to G. Bolz for "Indirect Solid Surface Test For Antigens or Antibodies", (directed to a specifically-described procedure for determining reacted labeled antibody);

4) Canadian Patent No. 1,107,195 issued Aug. 18, 1981 to D. Wagner et al for "Specific Binding Assay Employing Polystyrene As Separating Agent" (which provided a specific binding assay method using nonion-exchange cross-linked polystyrene for determining a ligand in, or the ligand-binding capacity of, a liquid medium);

5) Canadian Patent No. 1,108,986 issued Sept. 15, 1981 to D. Wagner et al for "Specific Binding Assay Employing Polyvinyl Alcohol As Separating Agent" (which provided a specific binding assay method using nonion-exchange cross-linked polyvinyl alcohol for determining a ligand in or the ligand binding capacity of a liquid medium);

6) Canadian Patent No. 1,152,430 issued Aug. 23, 1985 to J. Gordon et al for "Protein On Nitrocellulose Sheet Support" (directed to a solid support for proteins consisting of a porous nitrocellulose sheet containing an electrophoretically transferred replica of an electropherogram of proteins in a gel);

7) Canadian Patent No. 1,199,269 issued Jan. 14, 1986 to V. A. Marinkovitch for "Multiple Component Binding Assay System and Method of Making and Using it" (directed to a diagnostic kit which included a support having a plurality of cotton threads supported in a predetermined spaced relation for simultaneous contact with a liquid test sample);

8) U.S. Pat. No. 3,951,741 patented Apr. 20, 1976 by R. F. Devlin for "Sensitized Matrix For Detection of Disease" (directed to a specific sensitized matrix for diagnosing both infectious and non-infectious diseases, including an insoluble, inert, pliable and wettable matrix having a network of pores, and a protein polymer network immobilized in that network of pores);

9) U.S. Pat. No. 4,168,146 patented Sept. 18, 1979 by A. O. Grubb et al for "Immunoassay With Test Strip Having Antibodies Bound Thereto" (directed to a diagnostic test device useful for immunochemical quantification, which was a carrier strip comprising a silica-modified micro-porous polymer having finely-divided silica substantially-uniformly embedded in a particularly-recited permeable, continuous polymeric matrix);

10) U.S. Pat. No. 4,277,561 patented Jul. 7, 1981 by D. Monget et al for "Support For The Determination of Enzyme Activities and Process" (directed to a support for the determination of enzyme activity in a biological extract wherein the support comprised a fibrous material impregnated with a substrate and a particularly-recited water-soluble pH stabilizer);

11) U.S. Pat. No. 4,347,311 patented Aug. 31, 1982 by H. H. Schmitz for "Enzyme Immunoassay For Determining Antigen Specific Antibodies and Test Kit For Carrying Out This Assay" (directed to a highly sensitive enzyme immunoassay procedure for determining antibodies which are specific to antigens by coating a particularly-recited solid support with an antibody); and 12) U.S. Pat. No. 4,442,204 patented Apr. 10, 1984 by A. C. Greenquist for "Homogeneous Specific Binding Assay Device and Preformed Complex Method" (directed to a test device comprising a solid carrier member, e.g., a fibrous web matrix, e.g. paper, or a polymeric film or gel, incorporated with specifically-recited reagents for a homogeneous specific binding assay system).

SUMMARY OF THE INVENTION

Aims of the Invention

Accordingly, those concerned with the development and use of immunoassay techniques and related devices have recognized the desirability for further improvements and it is therefore one object of the invention to provide a rapid, accurate method for the quantitation of antigen or antibody on a solid surface.

A further object of the invention is to provide a method to provide rapid and sensitive immunoassays.

A still further object of the present invention is the provision of a relatively simple yet high effective and sensitive diagnostic test for the detection of specific disease states, both infectious and non-infectious.

Yet another object of this invention is the use of the macroporous hydrophobic cloths to make enzyme immunoassays rapid and simple.

Yet another object of this invention is to enable the use of macroporous hydrophobic cloths for enzyme immunoassays for antigens and haptens as well as for antibodies.

STATEMENTS OF INVENTION

By this invention, an enzyme immunoassay device is provided comprising the combination of (a) a macroporous hydrophobic synthetic polymer woven or non-woven cloth having a thickness of more than about 200 $\mu$m and having spaces between fibres exceeding about 20 $\mu$m in diameter, the cloth consisting entirely of unmodified hydrophobic threads formed of a synthetic polymer selected from the group consisting of polypropylene, polyester, nylon, and polyethylene; and (b) an unmodified antibody or an unmodified antigen directly adsorbed thereon and directly absorbed therein; the cloth having a Frazier Air Permeability in CFM/ft$^2$ at 0.5"H$_2$O of about 215 for a cloth of thickness about 40 mils, the cloth thereby having such porosity that it can accommodate a large volume of liquid per surface area thereof, that it has a large surface area for binding to the antibody or the antigen, respectively, and that it has minimum flow resistance.

The term "macroporous" as applied to cloths when used herein is intended to mean textiles composed of hydrophobic synthetic polymeric fibers, which are either woven or non-woven into a physically structurally stable cloth of more than about 200 $\mu$m thickness, such that the pores (i.e., spaces between the fibers) exceed about 20 $\mu$m in diameter.

The term "hydrophobic" as applied to cloths when used herein is intended to mean that the cloths repel water, the degree of repelling being dependent on the pore size and the inherent polymeric properties.

The term "unmodified" when referring to the hydrophobic threads is intended to mean that the threads have not been subjected to any chemical treating reaction, nor to any surface coating treatment.

The term "unmodified" when referring to the antibody or the antigens is intended to mean that neither the antibody nor the antigen have been subjected to any chemical treating reaction for the purpose, e.g. of enabling them to adsorb to the surface of the macroporous hydrophobic cloth.

The term "non-woven" when referring to the cloth is intended to mean a cloth formed from a random arrangement of natural or synthetic fibres by adhesives, heat and pressure, or needling techniques.

This invention also provides an enzyme immunoassay method for detecting an antigen comprising the steps of: a) treating a surface of an immunoassay device comprising a macroporous hydrophobic synthetic polymer woven or non-woven cloth having a thickness of more than about 200 μm and having spaces between fibres exceeding about 20 μm in diameter, the cloth consisting entirely of unmodified hydrophobic threads formed of a synthetic polymer selected from the group consisting of polypropylene, polyester, nylon, and polyethylene with an unmodified antibody, thereby to have an antibody directly adsorbed thereon and directly absorbed therein, the cloth having a Frazier Air Permeability in CFM/ft$^2$ at 0.5"H$_2$O of about 215 for a cloth of thickness about 40 mils, the cloth thereby having such porosity that it can accommodate a large volume of liquid per surface area thereof, that it has a large surface area for binding to the antibody and that it has minimum flow resistance, thereby to provide an antibody surface-treated cloth; b) applying, to the surface of the antibody surface-treated cloth, an antigen being assayed, thereby to provide an antigen-treated cloth; c) incubating the antigen-treated cloth with a sample to be tested for the antigen, thereby to provide an incubated cloth; d) washing the incubated cloth with a buffer to remove unadsorbed material, thereby to provide a washed cloth; e) incubating the washed cloth with an enzyme-antibody conjugate prepared by coupling purified antibody specific for the antigen to a suitable indicator enzyme, thereby to provide an incubated washed cloth; f) washing the incubated washed cloth with a buffer to remove unreacted conjugate; and g) detecting enzyme-antibody conjugate remaining thereon by incubation in a chromogenic substrate indicator solution to produce a visible colour upon product formation, indicative of the presence of an antigen.

This invention also provides an enzyme immunoassay method for detecting an antibody comprising the steps of: a) treating a surface of an immunoassay device comprising a macroporous hydrophobic synthetic polymer woven or non-woven cloth having a thickness of more than about 200 μm and having spaces between fibres exceeding about 20 μm in diameter, the cloth consisting entirely of unmodified hydrophobic threads formed of a synthetic polymer selected from the group consisting of polypropylene, polyester, nylon, and polyethylene with an unmodified antigen, thereby to have an antigen directly adsorbed thereon and directly absorbed therein, the cloth having a Frazier Air Permeability in CFM/ft$^2$ at 0.5"H$_2$O of about 215 for a cloth of thickness about 40 mils, the cloth thereby having such porosity that it can accommodate a large volume of liquid per surface area thereof, that it has a large surface area for binding to the antigen and that it has minimum flow resistance; thereby to provide an antigen surface-treated cloth; b) applying, to the surface of the antigen surface-treated cloth, an antibody being assayed, thereby to provide an antibody-treated cloth; c) incubating the antibody-treated cloth with a sample to be tested for the antibody, thereby to provide an incubated cloth; d) washing the incubated cloth with a buffer to remove unadsorbed material, thereby to provide a washed cloth; e) incubating the washed cloth with an enzyme-antibody conjugate prepared by coupling purified antibody specific for the antibody to a suitable indicator enzyme, thereby to provide an incubated washed cloth; f) washing the incubated washed cloth with a buffer to remove unreacted conjugate; and g) detecting enzyme-antibody conjugate remaining thereon by incubation in a chromogenic substrate indicator solution to produce a visible colour upon product formation, indicative of the presence of an antibody.

This invention also provides an enzyme immunoassay method for detecting an antibody comprising the steps of: a) treating an immunoassay device comprising a macroporous hydrophobic synthetic polymer woven or non-woven cloth having a thickness of more than about 200 μm and having spaced between fibres exceeding about 20 μm in diameter, the cloth consisting entirely of unmodified hydrophobic threads formed of a synthetic polymer selected from the group consisting of polypropylene, polyester, nylon, and polyethylene with an unmodified antibody, thereby to have an antigen directly adsorbed thereon and directly absorbed therein, the cloth having a Frazier Air Permeability in CFM/ft$^2$ at 0.5"H$_2$O of about 215 for a cloth of thickness about 40 mils, the cloth thereby having such porosity that it can accommodate a large volume of liquid per surface area thereof, that it has a large surface area for binding to the antibody and that it has minimum flow resistance, thereby to provide an antibody surface-treated cloth; b) applying to the surface of the antibody surface-treated cloth, a mixture of the antibody being assayed and an enzyme-antigen conjugate specific for the antibody adsorbed onto the cloth, thereby to provide an antibody/enzyme-antigen conjugate treated cloth; c) applying, to the surface of a control cloth identical to the hydrophobic synthetic polymer cloth, the same enzyme-antibody conjugate, thereby to provide an enzyme-antigen conjugate treated control cloth; d) incubating both the antibody/enzyme-antibody conjugate treated cloth and the enzyme-antigen conjugate treated control cloth substantially simultaneously, to provide incubated cloths; e) washing both the incubated antibody/enzyme-antigen conjugate treated cloth and the incubated enzyme-antigen conjugate treated control cloth with a buffer solution; and f) detecting the antibody by incubation of both the washed antibody/enzyme-antigen conjugate treated cloth and the washed enzyme-antigen conjugate treated control cloth in a chromogenic substrate indicator solution to produce a visible colour upon product formation indicative of the presence of antibody, the amount of antibody being determined by the difference in intensity of the colour on the antibody/enzyme-antigen conjugate treated cloth and the colour on the enzyme-antigen conjugate treated control cloth.

This invention also provides an enzyme immunoassay method for detecting an antigen comprising the steps of: a) treating an immunoassay device comprising a macroporous hydrophobic synthetic polymer woven or non-woven cloth having a thickness of more than about 200 μm and having spaced between fibres exceeding about 20 μm in diameter, the cloth consisting entirely of unmodified hydrophobic threads formed of a synthetic polymer selected from the group consisting of polypropylene, polyester, nylon, and polyethylene with an unmodified antibody, thereby to have an antibody directly adsorbed thereon and directly absorbed therein, the cloth having a Frazier Air Permeability in CFM/ft$^2$ at 0.5"H$_2$O of about 215 for a cloth of thickness about 40 mils, the cloth thereby having such porosity that it can accommodate a large volume of liquid per surface area thereof, that it has a large surface area for binding to the antibody and that it has minimum flow resistance, thereby to provide an antibody surface-treated cloth; b) applying to the surface of the antibody surface-treated cloth a mixture of the antigen being assayed and an enzyme-antibody conjugate specific for the antigen, thereby to provide an enzyme-antibody conjugate treated cloth; c) applying, to the surface of a control cloth identical to the hydrophobic synthetic polymer cloth, the same enzyme-antibody conjugate, thereby to provide an enzyme-antibody conjugate treated control cloth; d) incubating both the antigen/enzyme-antibody conjugate treated cloth and the enzyme-antibody conjugate treated control cloth substantially simultaneously to provide incubated cloths; e) washing both the incubated antigen/enzyme-antibody conjugate treated cloth and the incubated enzyme-antibody conjugate treated control cloth with a buffer solution; and f) detecting the antigen by incubation of both the antigen/enzyme-antibody conjugate treated cloth and the enzyme-antibody conjugate treated control cloth in a chromogenic substrate indicator solution to produce a visible colour upon product formation, indicative of the presence of antigen, the amount of antigen being determined by the difference in intensity of the colour on the antigen/enzyme-antibody conjugate treated cloth and the colour on the enzyme-antibody conjugate treated control cloth.

OTHER FEATURES OF THE INVENTION

By another feature of this invention, the enzyme immunoassay device may be so-treated with an antiserum containing an antibody specific for the antigen being tested, or by still another feature of this invention, it may be so-treated with a purified antibody bearing the appropriate specificity. By yet another feature of this invention, the antibodies present in the antiserum may be partially denatured prior to being so-applied to the hydrophobic cloth, e.g. by exposure to a low pH environment, e.g, a pH of about 2.5, or by heating. Alternatively, by yet a further feature of this invention, the antibodies may be affinity-purified prior to being so-applied to the hydrophobic cloth. By still another feature of this invention, the antibody may be provided by diluted antiserum.

By yet another feature of this invention, the enzyme immunoassay device of the invention may be in the form of the macroporous hydrophobic cloth bonded to a different material, thereby to provide an antibody-coated or antigen-coated test strip that may be handled throughout an assay procedure. Thus, the present invention embraces the bonding, in any suitable manner, of the so-treated macroporous hydrophobic cloth to a dipstick.

GENERALIZED DESCRIPTION OF THE INVENTION

It has surprisingly been found that all macroporous hydrophobic cloths (as defined above) when coated with an unmodified antigen or antibody (as defined above) provide an unexpected improvement in the enzyme immunoassay procedure of the present invention. All such macroporous hydrophobic cloths, whether they be formed of polypropylene, nylon, polyester or polyethylene threads, have the following characteristics: they can accommodate a larger volume of sample per area; they have a larger surface area for binding immunoreactants and for immunoreactions; they are easily washed because of minimum flow resistance; and they have both strength and durability. Thus, it has been found that the macroporous hydrophobic cloths used as supports in the enzyme immunoassay methods of this invention provide a large volume for absorption per surface area for antigen-antibody interaction. Macroporous polypropylene, polyethylene, nylon, and polyester cloths, by virtue of their hydrophobic characteristics, have been found to adsorb and absorb antibodies and thus provide a large surface area for antigen capture. Macroporous cloths all have such minimum flow resistance.

Such macroporous hydrophobic cloths made of, e.g. polypropylene and polyester, are readily commercially available and are moderately priced because of their large commercial demand as textiles and filters. Macroporous 100% nylon cloth is commercially available as a generic product and was acquired locally in the Ottawa, Canada area. Macroporous woven polyester cloth is commercially available as a generic product and was acquired locally in the Ottawa, Canada area. Macroporous non-woven polypropylene filter cloth is available as a generic product and was purchased from Aldrich Chemical Co. A variety of non-woven, macroporous polyester cloths were obtained from DuPont, and is known by the trademark SONTARA.

One preferred embodiment of such SONTARA is SONTARA 8100 ™, which has the following chemical and physical characteristics.

Typical Physical Properties of SONTARA 8100 are:

| | UNIT WEIGHT (oz/yd$^2$) | THICKNESS (mils) | SHEET GRAB TENSILE (lbs) | | TRAPEZOID TEAR (lbs) | | MULLEN BURST (psi) | FRAZIER AIR PERMEABILITY (CFM/ft$^2$ @ 0.5" H$_2$O) | ROLL SIZE (7" ID CORE) | |
|---|---|---|---|---|---|---|---|---|---|---|
| | | | MD | XD | MD | XD | | | in. O.D. | lin. yds. |
| Style 100% Polyester 8100 | 40 | 40 | 70 | 45 | 35 | 40 | 120 | 215 | 44 | 1700 |

Frazier Air Permeability is described in ASTM D737 75, the contents of which are hereby incorporated by reference.

It has been found that the use of macroporous hydrophobic cloths also provide improvements in the sensitivity of antiserum-based enzyme immunoassay. These improvements are consequence of an increase in the hydrophobicity of the denatured Fc region of the antibodies, which in turn causes these to be adsorbed more strongly to the hydrophobic cloth surface and in greater numbers. The partially-denatured state may also ensure that the antibodies adhere to the solid phase in a more ideal orientation, with the Fc region.

Consequently, the enzyme immunoassay procedure of one embodiment of this invention may consist of the following: a macroporous hydrophobic cloth having such porosity that it can absorb and adsorb a large volume of liquid per surface area of the cloth, is treated to have adsorbed and absorbed thereon and therein, either an antiserum containing antibody specific for the antigen being tested, or a purified antibody bearing the appropriate specificity, and is subsequently incubated with the test sample purported to contain the antigen. The macroporous hydrophobic cloth is then washed with an appropriate buffer to remove any unadsorbed and unabsorbed material, and is then incubated with an enzyme-antibody conjugate prepared by coupling purified antibody specific for the antigen to a suitable indicator enzyme. The macroporous hydrophobic cloth is then washed with buffer to remove unreacted conjugate. and the remaining conjugate is detected by incubation in a chromogenic substrate-indicator solution which produces a visible colour upon product formation.

The enzyme immunoassay procedure of another embodiment of the invention may consist of the following: a test sample containing the antigen to be assayed is mixed with a suitable enzyme-antibody conjugate, e.g. diluted horseradish peroxidase (HRP)-antibody conjugate specific for the antigen of interest, and an aliquot of this mixture is incubated with an antigen-treated hydrophobic cloth. A control macroporous hydrophobic cloth is treated with a mixture of the same enzyme-antibody conjugate but without the free antigen.

After washing with a suitable buffer solution, e.g. PBST, macroporous hydrophobic cloths incubated with an antigen-conjugate mixture fail to produce the same intensity of colours (upon incubation in ABTS-indicator) as macroporous hydrophobic cloths incubated with a control mixture consisting of the conjugate in the absence of free antigen.

While it is not desired to be bound by any theory, it is believed that antigen present in the test sample combines with the conjugate, thus preventing its interaction with the antigen-treated cloth. In this manner, the presence of antigen in a test sample will diminish the amount of colour produced in the test, while the control sample (minus free antigen) gives proof of the functional integrity of the conjugate.

The detection of B. abortus antigen LPS, using the enzyme immunoassay with LPS-coated macroporous polyester cloth has thus been provided as another embodiment of this invention. The enzyme immunoassay, which requires only one incubation with the immunological reagent, provides an internal control for the quality of the reagent used.

Before describing various embodiments of this invention, a description of the reagents used will be given. Chemicals used were of the analytical reagent grade. All biochemicals were purchased from Sigma Chemical Co. Distilled water ($H_2O$) was employed as a universal solvent. Antigens and bovine antisera were provided by the Animal Diseases Research Institute (ADRI) in Nepean, Ontario, Canada. Some materials employed as solid phases (i.e. cellulose cotton and nylon cloths) were commercially available as generic materials and were acquired locally, in the Ottawa, Canada area, whereas non-woven polypropylene filter cloth was commercially available as a generic product and was purchased from Aldrich Chemical Co. and a variety of polyester cloths were commercially available under the trademark SONTARA and were obtained from DuPont.

Enzyme Immunoassay Reagents

| | |
|---|---|
| (1) 0.06M carbonate buffer (pH 9.6) | |
| $NaHCO_3$ | 3.8 g |
| $Na_2CO_3$ | 1.93 g |
| Add $H_2O$ and NaOH (if necessary) to 1,000 ml. | |
| (2) 0.01M phosphate-buffered saline (pH 7.2) (PBS) | |
| $NaH_2PO_4.2H_2O$ | 0.31 g |
| $Na_2HPO_4$ | 1.1 g |
| NaCl | 8.5 g |
| (3) PBS with TWEEN 20 (PBST) | |
| PBS | 1000 m |
| TWEEN 20 [TWEEN 20 is the registered Trade Mark of an emulsifier comprising polyoxyethylene derivatives of fatty acid partial esters of sorbitol anhydrides of Atlas Chemical Industries] | 0.5 ml |
| (4) Indicator system for horseradish peroxidase (ABTS-indicator) | |
| 0.05M citrate buffer (pH 4.5) | 20 ml |
| 40 nM 2,2'-Azino-di-(3-ethylbenzthiazoline sulfonic acid) (ABTS) | 0.5 ml |
| 0.5M $H_2O_2$ | 0.02 ml |
| (5) Indicator system for alkaline phosphatase | |
| diethanolamine | 2.62 g |
| P-nitrophenyl phosphate | .025 g |

Add $H_2O$ and HCl to 25 ml to obtain a final pH 9.8.

Preparation of Affinity Purified Anti-Brucella Antibodies from Bovine Antiserum Anti-Brucella antibodies were purified from bovine antiserum by the affinity purification method. It is based on the adsorption of anti-Brucella antibodies onto the antigenic surface of whole killed *B. abortus* cells mixed with antiserum. Cells with adsorbed antibodies can then be separated from the serum by centrifugation, and the antibodies can be recovered by exposure to a low pH environment with subsequent removal of the cells by centrifugation. The method is simple to perform, inexpensive, and usually results in high yields of specific antibodies.

Ten milliliters of standard plate test antigen, consisting of whole heat-killed *B. abortus* cells (strain 413, biotype 1) suspended in phenol-saline (i.e., 0.85% NaCl and 0.5% phenol in $H_2O$) at a concentration of 4×10'' cells/ml, were dispensed in a 50 ml-capacity round bottom polycarbonate centrifuge tube. The cells were pelleted by centrifugation at 10,000×g, for 10 minutes. The pellet was then washed twice in 0.1M glycine-HCl (pH 2.24) to remove any acid-soluble material present on the cell surface, followed by two washings in 0.1M Tris-HCl buffer (pH 7.0). Care was taken to disperse the cells as gently as possible during resuspension (a glass stirring rod is convenient for this purpose). To the final washed pellet was added 25 ml of bovine antiserum, in which the cells were dispersed. The suspension was allowed to stand at room temperature for 30–40 minutes, with gentle stirring every 5–10 minutes. The suspension was then centrifuged as above and the supernatant discarded. The resulting pellet was washed three times in 25 ml of 0.1M Tris-HCl buffer (pH 7.0) to remove any loosely adsorbed material. Brucella-specific antibody was recovered by resuspending the final washed pellet in 25 ml of 0.1M glycine-HCl (pH 2.24). The cells were immediately removed by centrifugation and antibody-rich supernatant was transferred to a vessel containing 10 ml of 1.0M Tris-HCl buffer (pH 8.0) in order to abrogate the harsh low pH environment. The remaining cell pellet was processed in this manner a second time to improve antibody recovery, and the final supernatants were pooled. The antibody solution was then dialyzed against PBS for 24 hours at 4° C., with at least three changes of buffer. Precipitate material arising in the dialysate was stored at −80° C. until use. Whenever necessary, the protein in the dialysate was concentrated using an Amicon protein concentrator.

Unless otherwise specified, antiserum used in the Examples was serum obtained from chronically infected cattle which have high titers of anti-Brucella antibody. *B. abortus* cells used were heat-killed standard plate test antigen (whole cells) which is strain 413, biotype 1, suspended in phenol-saline.

Preparation of an Enzyme-antibody Conjugate by the Periodate Oxidation Method

A modified version of the method developed by Nakane and Kawaoi was employed for conjugating horseradish peroxidase with anti-Brucella antibody. For this, highly purified horseradish peroxidase (RZ=3) was used, where RZ is the light absorbance ratio of $A_{403}/A_{275}$ for a given enzyme solution. Five milligrams of horseradish peroxidase (Sigma, type VI, RZ=3.0) were dissolved in a mixture of 1.0 ml of 0.3M sodium carbonate (pH 8.1) and 1.0 ml of 0.08M $NaIO_4$. The solution was mixed gently for 30 minutes at room temperature, and 1.0 ml of 0.16M ethylene glycol was then added. This was further mixed at room temperature for 1 hour. The latter solution was then dialyzed against 5 l of 0.01M sodium carbonate buffer (pH9.5) at 4° C. for 16–24 hours. To this dialysate was added 0.5 ml of PBS containing ca. 5 mg of affinity purified anti-Brucella antibody and 0.5 ml of 1.01M carbonate buffer (pH 9.5). The solution was incubated for 3 hours at room temperature, with gentle mixing. At the end of the incubation, 5 mg of $NaBH_4$ were added to the solution which was then left to stand at 4° C. for 3 hours. The solution was then dialyzed extensively against PBS at 4° C. Any precipitable material formed in the dialysate was removed by centrifuging for 10 minutes in an eppendorf microfuge. The resulting supernatant constituted the stock conjugate, which was designated conjugate, and was stored at −20° C. until use.

Collection of Antiserum

An adult cow suffering from chronic brucellosis was bled at one-week intervals over a period of approximately three weeks. At each bleeding, ca. 1 l of blood was collected in glass bottles and immediately incubated at 37° for 2 hours, followed by overnight storage at 4° C. to allow for complete clot formation. The serous liquid was decanted into separate vessel and centrifuged at 8,000×g to remove any remaining blood cells. The supernatant thus obtained was stored at −20° C.

A large stock of antiserum, which was used as a source of antibody for all subsequent experiments, was prepared by pooling all serum samples obtained after the prescribed succession of bleedings, and was stored at −80° C. until use.

BRIEF DESCRIPTION OF THE DRAWINGS

In the accompanying drawings,

FIG. 1 is a graph showing the effect of varying the treating concentration on the signal generated in the polypropylene cloth-based cloth enzyme immunoassay;

FIG. 2 is a graph showing the partial denaturation of bovine antiserum antibodies by audification;

FIG. 3 is a graph showing the partial denaturation of bovine antiserum and affinity purified antibodies by heat; and FIG. 4 is a graph showing diluted antiserum as a source of coating antibody.

DESCRIPTION OF PREFERRED EMBODIMENTS

The following are Examples of this invention:

I(a) Determination of the Optimum Affinity Purified Coating Antibody Concentration for Enzyme Immunoassay Using Macroporous Polypropylene cloth Macroporous polypropylene filter cloth pieces (6×6 mm) were coated with 50 μl of various concentrations of affinity purified anti-Brucella antibody per piece (a concentration range of 0.2 to 1.0 mg of protein/ml was chosen). After the required overnight incubation period, the cloths were washed with PBST and subsequently incubated with 30 μl of *B. abortus* cells (strain 413, biotype 1) diluted to $4\times10^8$ cells/ml in PBS, for 30 minutes at room temperature. A series of negative control cloths (incubated without antigen) was also included. The macroporous hydrophobic cloths were then washed with PBST and probed with 25 μl of conjugate diluted 1:1,000 in PBST, and incubated for 30 minutes at room temperature. After washing with PBST, the macroporous hydrophobic cloths were assayed for retained horseradish peroxidase activity by immersion in 0.5 ml of ABTS-indicator solution for 30 minutes, at room temperature, and the reaction was stopped by addition of 0.5 ml of 0.1M NaF. Absorbance was read at 650 nm.

As shown in FIG. 1, the assay response peaks at a concentration of 0.2 mg/ml.

I(b) Pretreatment (Partial Denaturation) of the Coating Antibody

The use of antiserum for the direct coating of the macroporous hydrophobic cloth was investigated as an effective and economical alternative to purified antibody.

In order to achieve maximum immobilization of the antibodies present in the antiserum, a simple procedure was developed for the pretreatment of the coating antiserum to incur partial denaturation of the antibodies, thus rendering them more capable of interacting with the macroporous hydrophobic cloth surface, to the exclusion of other serum proteins which might compete for binding sites on the cloth. In order to improve the detectability of the enzyme immunoassay employing bovine antiserum as the source of coating antibody, partial denaturation procedures were developed using an acidic pH and heat. The following describes an investigation undertaken to determine the optimum time of exposure to a pH 2.5 environment for the improved immobilization of antibodies from antiserum on macroporous polypropylene cloth.

Three separate 0.85 ml aliquots of antiserum were mixed with 0.3 ml each of 0.4M glycine-HCl buffer (pH 1.5) to produce a final pH 2.5. A zero-time exposure sample consisting of 0.85 ml of antiserum plus 0.6 ml of 1.0M Tris-HCl buffer (pH 7.0) was also prepared as a control. Each acidified sample was allowed to stand at room temperature for either 5, 10, or 20 minutes, after which they were immediately neutralized by addition of 0.3 ml of 1.0M Tris-HCl (pH 8.0). These samples were then used to coat macroporous polypropylene filter cloth pieces. The effect of time of exposure to pH 2.5 on the cloth enzyme immunoassay signal generated is presented in FIG. 2.

Figure 2:
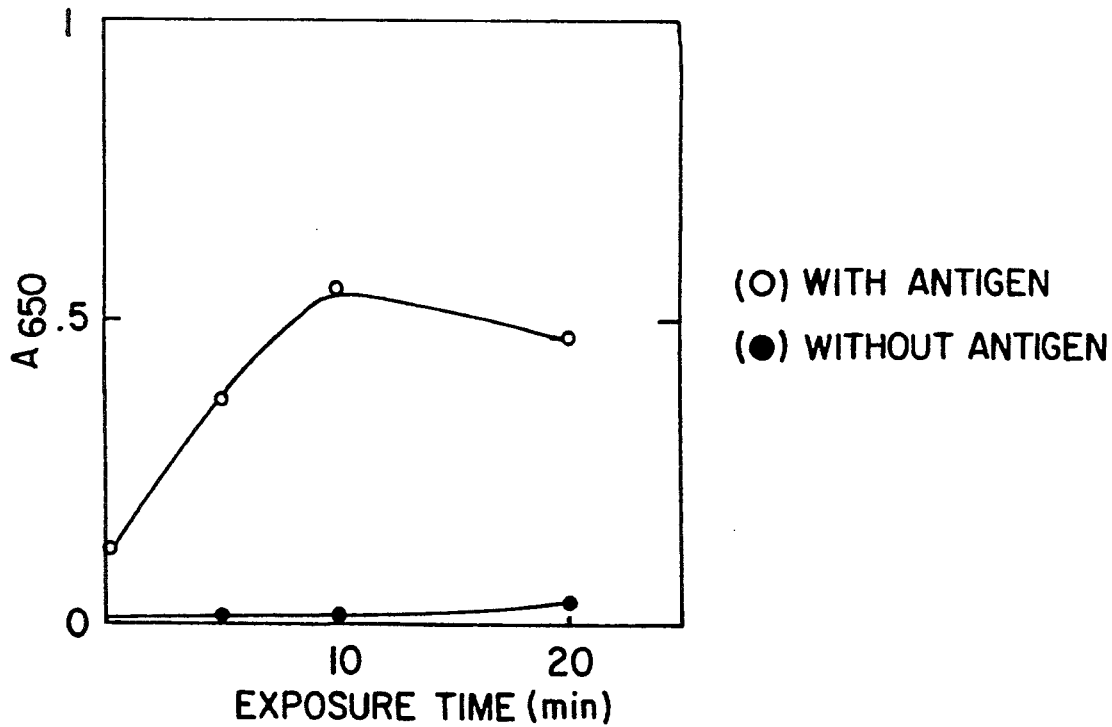
Figure 3:
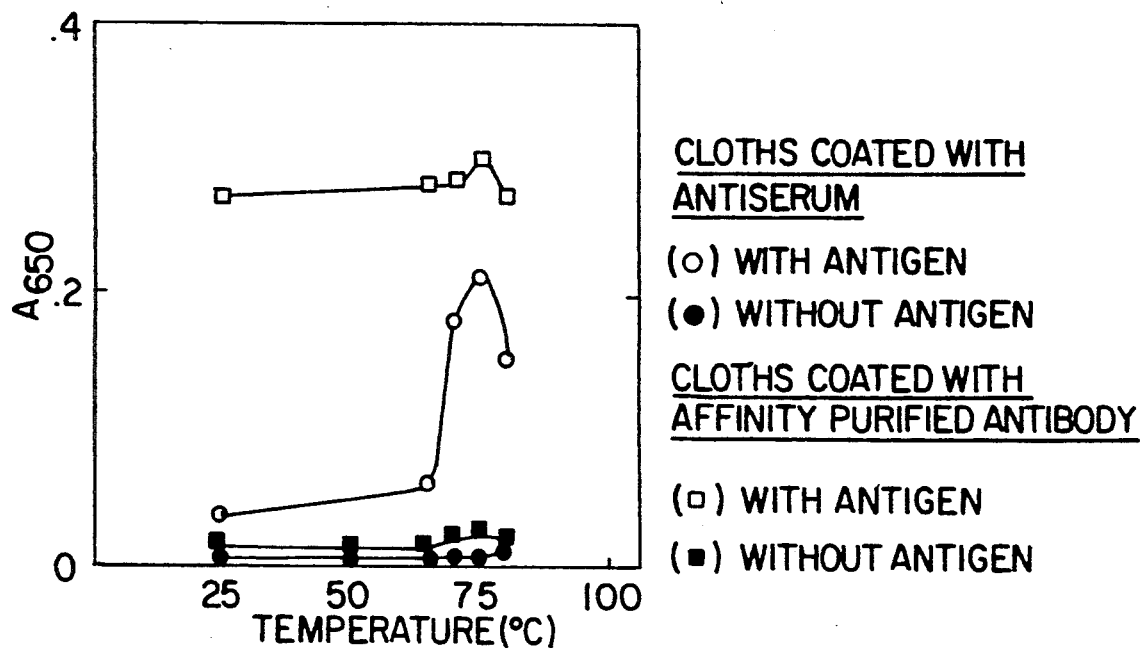
Figure 4:
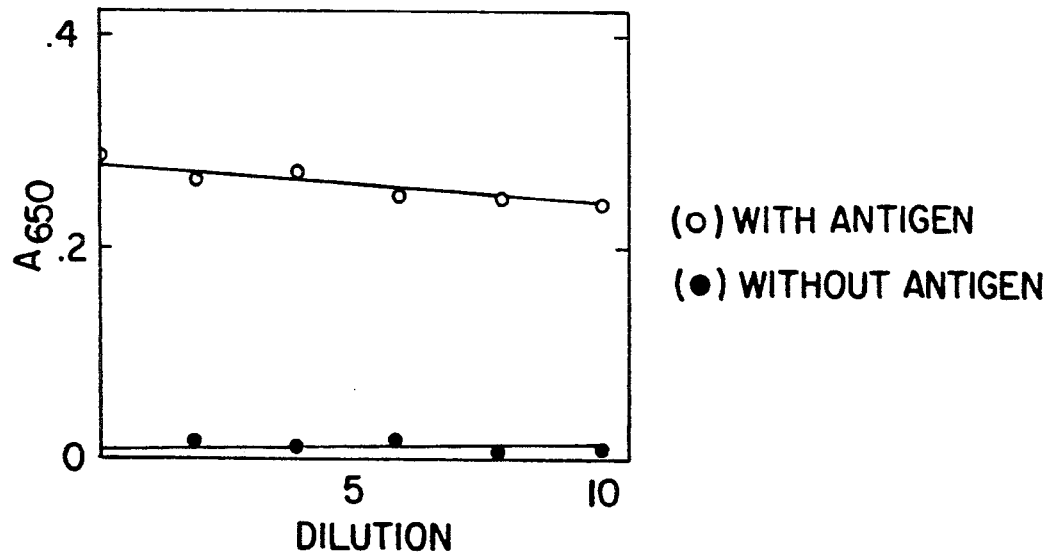

FIG. 2 shows that an approximate five-fold improvement in the assay's sensitivity was achieved by exposure of the antiserum to pH 2.5 for 10 minutes.

In a second experiment, the effect of exposing bovine antiserum and affinity purified antibodies to heat on their abilities to serve as sources of coating antibodies was examined. One milliliter samples of antiserum and the affinity purified antibody dialysate (containing 0.27 mg of protein/ml) were incubated for 10 minutes at either 25°, 65°, 70°, 75°, or 80° C. These were then allowed to cool to room temperature and used to coat macroporous polypropylene cloths as previously described. The enzyme immunoassay protocol employed was the same as in the previous experiment, with the exception that the antibody-coated macroporous hydrophobic cloths were incubated with 30 μl of $B.$ $abortus$ plate test antigen diluted to $4\times10^7$ cells/ml in PBS. The results of this experiment are presented in FIG. 3, where the signal generated in the enzyme immunoassay is plotted against temperature for both antiserum and affinity-purified antibody.

FIG. 3 shows that an even greater improvement in sensitivity was obtained by heating the serum at 75° C. for 10 minutes. The sensitivity of the enzyme immunoassay employing affinity purified antibody remained essentially unchanged over the range of temperatures tested.

These experiments have demonstrated the usefulness of either exposure to a low pH or heat in improving the sensitivity of the assay using antiserum as the source of coating antibody.

Without wishing to be bound by theory, it is believed that the improvement in the sensitivity of the antiserum-based immunoassay is a consequence of an increase in the hydrophobicity of the denatured Fc region of the antibodies, which in turn causes these to be adsorbed more strongly to the hydrophobic cloth surface and in greater numbers. The partially denatured state may also ensure that the antibodies adhere to the solid phase in a more ideal orientation, with the Fc region affixed to the cloth surface and the Fab segments free to interact with the antigen. Treating the affinity-purified antibodies with heat did not seem to confer any particular advantage. Thus, these affinity-purified antibodies cannot be beneficially altered further by heat treatment.

I(c) Diluted Bovine Antiserum as a Source of Coating Antibody

The feasibility of applying diluted antiserum in the enzyme immunoassay was investigated in the following experiment.

Aliquots of bovine antiserum were diluted 2, 4, 6, 8, and 10 times in PBS. The diluted samples were partially denatured by heating at 75° C. for 10 minutes. These were then cooled to room temperature and applied to 6×6 mm macroporous polypropylene filter cloth pieces, which were subsequently employed in the enzyme immunoassay according to the procedure used in the previous example. The results are presented in FIG. 4, where the enzyme immunoassay signal generated is plotted against the serum dilution factor.

FIG. 4 shows that there was no appreciable decline in the sensitivity of the assay throughout the range of coating serum dilutions examined. Therefore, it was concluded that bovine antiserum diluted 1:10 in PBS, with subsequent heating at 75° C. for 10 minutes, can serve as a suitable source of coating antibody in the enzyme immunoassay. The precise dilution factor used for a given batch of antiserum will, of course, depend on the specific antibody titer of that serum.

(II) Detectability of the Enzyme Immunoassay For Brucella Antigens

The detectability of Brucella cells and lipopolysaccharide antigens (LPS) by the macroporous polypropylene enzyme immunoassay was examined in this Example. Unless otherwise stated, all antibody-coated cloths used in the following experiments were prepared with bovine antiserum diluted 1:lo in PBS and heated at 75° C. for 10 minutes.

II(a) Detectability of the Whole Cell Assay Employing Antibody Coated Macroporous Polypropylene Filter cloth Antibody-coated macroporous polypropylene filter cloth pieces were incubated for 30 minutes at room temperature with 30 μl of *B. abortus* cell suspensions containing either $1.2\times10^5$, $1.2\times10^4$, or $1.2\times10^3$, cells in PBS. Each macroporous hydrophobic cloth in this series of experiments was prepared in quadruplicate, as were macroporous hydrophobic cloths to which 30 μl of PBS containing no antigen was added. These were then washed with PBST and probed with 25 μl of conjugate diluted 1:1000 in PBST, for 30 minutes at room temperature. At the end of this period, the macroporous hydrophobic cloths were washed with PBST and assayed for retained horseradish peroxidase by immersion in ABTS-indicator solution for 3 hours, in order to optimize the final enzyme signal. The enzyme reaction was stopped by addition of 0.5 ml of 0.1M NaF. Table 1 shows the relationship between the quantity of antigen added and the corresponding cloth enzyme immunoassay signal obtained.

TABLE 1

Detectability of the Whole Cell Assay Employing Antibody-Coated Macroporous Polypropylene Filter Cloth

| No. of Cells Applied Per Cloth | $A_{650}$ 1 | 2 | 3 | 4 |
|---|---|---|---|---|
| $1.2\times10^5$ | 0.186 | 0.213 | 0.234 | 0.245 |
| $1.2\times10^4$ | 0.107 | 0.080 | 0.106 | 0.075 |
| $1.2\times10^3$ | 0.054 | 0.050 | 0.060 | 0.055 |
| 0 | 0.060 | 0.051 | 0.058 | 0.055 |

Table 1 shows that the macroporous polypropylene cloth immunoassay can detect $10^4$ cells using a 36 $mm^2$ polypropylene cloth.

II(b) Detectability of Brucella LPS by Enzyme Immunoassay Using Macroporous Polypropylene Cloth The assay procedure employed for the detection of whole cells using antibody-coated macroporous polypropylene filter cloth was applied to the detection of *B. abortus* LPS. In this Example, antibody-coated macroporous hydrophobic cloths were incubated for 30 minutes at room temperature with 30 μl of PBS containing either 3, 0.3, or 0.03 ng of LPS, or PBS alone. Each macroporous hydrophobic cloth was prepared in quadruplicate. These were then processed in the immunoassay as previously described. The results are presented in Table 2.

TABLE 2

Detectability of LPS by Enzyme Immunoassay Using Macroporous Polypropylene Cloth

| LPS Applied per Cloth (ng) | $A_{650}$ | | | |
|---|---|---|---|---|
| | 1 | 2 | 3 | 4 |
| 3.00 | 1.350 | 1.302 | 1.440 | 1.100 |
| 0.30 | 0.261 | 0.225 | 0.216 | 0.230 |
| 0.03 | 0.063 | 0.058 | 0.066 | 0.068 |
| 0 | 0.068 | 0.040 | 0.043 | 0.056 |

Table 2 shows that the detectability of this enzyme immunoassay occurred at approximately 0.3 ng (or 300 picograms) of LPS applied per macroporous hydrophobic cloth piece.

II(c) Performance of the Enzyme Immunoassay Under Simulated Clinical Conditions

In the routine diagnosis of brucellosis, Brucella organisms are often recovered from infected animals in milk; vaginal secretions; supramammary, retropharyngeal, internal iliac, and lumbar lymph nodes; spleen tissue; uterine tissue; and in some instances, blood. As these materials constitute complex environments for the detection of antigens, it was determined whether or not undefined sample components might be prohibitive to antigen detection by the enzyme immunoassay. Another aspect of clinical specimens examined was the interference of anti-Brucella antibodies present in the samples to the antigen assay by the enzyme immunoassay. The ability of the macroporous polypropylene filter cloth-based enzyme immunoassay to detect *B. abortus* antigens in body fluids and tissue homogenates of bovine origin was examined in Example II. Antibody-coated cloth was prepared as in the previous Example.

II(d) Detection of *B. Abortus* in Bovine Body Fluids and Tissue Homogenates

In order to ascertain the ability of the enzyme immunoassay to detect *B. abortus* antigens in simulated clinical specimens, tissues obtained from a cow which was a serological reactor for *B. abortus,* but culture negative, were artificially innoculated with whole cells and assayed for the presence of antigen as described below. The presence of endogenous circulating antibody specific for *B. abortus* offered an opportunity to assess the performance of the assay under conditions which might theoretically interfere with the capture of antigen in such samples. The possible inhibitory effect of endogenous antibody was alleviated by subjecting the test samples to extreme heat (3 hours, 70° C.) prior to performing the assay.

Tissue homogenates were prepared by homogenizing in a stomacher and adding sufficient PBS to produce a fluid consistency (approximately 0.5 ml per gram of tissue). Homogenates were made from the following bovine tissues; inguinal lymph nodes, spleen, and uterine horn.

A sample from each homogenate was inoculated with sufficient *B. abortus* cells to give a final concentration of $8\times10^5$ cells/ml Milk and serum samples from a healthy animal were likewise inoculated. These samples, along with their uninoculated counterparts, were heated at 70° C. for 3 hours, after which they were cooled to room temperature. Antibody-coated macroporous polypropylene filter cloths were then added to triplicate test tubes containing 0.5 ml of heated sample (one macroporous hydrophobic cloth/tube) and incubated for 30 minutes at room temperature with constant gentle shaking. The macroporous hydrophobic cloths were then removed and processed in the enzyme immunoassay as previously described. Macroporous hydrophobic cloths were assayed for retained conjugate by immersion in 0.5 ml of ABTS-indicator solution for 30 minutes. The results are shown below in Table 3.

TABLE 3

Detection of Antigens Suspended in Body Fluids and Tissue Homogenates.

| | $A_{650}$ | | | | | |
|---|---|---|---|---|---|---|
| | Specific[b] | | | Control[c] | | |
| Sample[a] | 1 | 2 | 3 | 1 | 2 | 3 |
| A | 0.185 | 0.240 | 0.224 | 0.070 | 0.090 | 0.083 |
| B | 0.164 | 0.177 | 0.170 | 0.057 | 0.060 | 0.061 |
| C | 0.132 | 0.170 | 0.162 | 0.022 | 0.027 | 0.020 |
| D | 0.159 | 0.165 | 0.162 | 0.020 | 0.030 | 0.020 |
| E | 0.175 | 0.192 | 0.195 | 0.045 | 0.042 | 0.040 |

[a]Tissue homogenates from spleen (A), inguinal lymph nodes (B), unterine hore (C), plus, normal bovine serum (D) and normal bovine milk (E).
[b]Cloths incubated with inoculated samples.
[c]Cloths incubated with uninoculated samples.

Table 3 demonstrates the assay response for each sample tested In most cases, the control signals (i.e., those obtained from the uninoculated samples) remained low, whereas those arising from the corresponding inoculated samples were distinct. The experiment demonstrates the ability of the enzyme immunoassay to detect *B. abortus* antigens suspended in various biological samples.

III Detection of Bovine Viral Diarrhea (BVD) Antigen

The applicability of the ability of the enzyme immunoassay to detect antigens of bacterial origin to the detection of viral antigens will now be described in this Example.

Bovine viral diarrhea is an enteric disease posing a serious threat to exposed livestock. The etiological agent is a virus which is referred to as bovine viral diarrhea (BVD) antigen. At present, an enzyme immunoassay method is not used for the detection of BVD antigen in clinical specimens.

The strategy employed for the BVD assay was similar to that used previously for the detection of Brucella antigens macroporous polypropylene filter cloth was coated with anti-BVD antibodies and subsequently incubated with BVD antigen, and the captured material was detected by probing with an enzyme-antibody conjugate (prepared by coupling antibodies from anti-BVD antiserum to horseradish peroxidase by the periodate oxidation method). Whole antiserum was employed in order to make the required conjugate. The feasibility of using whole antiserum for this purpose was first tested by conjugating whole anti-Brucella antiserum with horseradish peroxidase and applying the resulting conjugate in the *B. abortus* enzyme immunoassay, thus affording an opportunity to compare the performance of such a conjugate with an established system.

III(a) Synthesis and Testing of a Brucella-specific Enzyme-Antibody Conjugate Made With Whole Bovine Antiserum Whole bovine anti-Brucella antiserum was conjugated to horseradish peroxidase according to the periodate oxidation method: 0.5 ml of whole serum was dialyzed overnight at 4° C. against 0.01M sodium carbonate buffer (pH 9.5). The resulting dialysate was mixed with 5 mg of periodate-activated horseradish peroxidase and incubated for 2.5 hours at room temperature. Sodium borohydride ($NaBH_4$) was then added as prescribed, and incubated for 3 hours at 4° C. against PBS, and the final dialysate was microfuged (10 minutes, at 4° C.). The cleared dialysate constituted the conjugate stock.

The performance of this conjugate in the immunoassay was compared to that of the conjugate prepared with purified antibody. Two series of Brucella-specific antibody-coated macroporous polypropylene filter cloth pieces were incubated with 30 μl of *B. abortus* cells diluted to $4 \times 10^8$, $4 \times 10^7$, or $4 \times 10^6$ cells/ml in PBS, for 30 minutes at room temperature. The macroporous hydrophobic cloths were then washed in PBST, and one series was probed with 25 μl of the conjugate prepared with affinity purified antibody diluted 1:100 in PBST while the other series was probed with 25 μl of the conjugate prepared with whole antiserum diluted 1:100 in PBST. These were incubated for 30 minutes, at room temperature, and subsequently washed with PBST. The macroporous hydrophobic cloths were assayed by immersion in 0.5 ml of ABTS-indicator solution for 30 min. The results are shown below in Table 4.

TABLE 4

Relative Performance of Conjugate D in the Enzyme Immunoassay.

| No. of Cells Applied per Cloth | conjugate[1]* $A_{650}$ | | conjugate[2]** | |
|---|---|---|---|---|
| | 1 | 2 | 1 | 2 |
| $1.2 \times 10^7$ | 0.852 | 0.932 | 0.631 | 0.598 |
| $1.2 \times 10^6$ | 0.385 | 0.400 | 0.153 | 0.180 |
| $1.2 \times 10^5$ | 0.081 | 0.092 | 0.081 | 0.080 |
| 0 | 0.010 | 0.012 | 0.070 | 0.075 |

*prepared by coupling affinity purified antibody to HRP
**prepared by coupling whole antiserum to HRP According to Table 4, the response of the enzyme immunoassay using conjugate[2] was somewhat dampened throughout the series of antigen dilutions tested, as compared to the performance of conjugate[1] in the assay. However, the Example demonstrates the feasibility of employing such a conjugate.

III(b) Adapted Enzyme Immunoassay for the Detection of BVD Antigen

A BVD-specific conjugate was prepared by coupling whole anti-BVD antiserum to horseradish peroxidase, in order to adapt the enzyme immunoassay for the direct detection of BVD antigen.

A sample of anti-BVD antiserum (precise titer unknown) was obtained from a cow vaccinated with killed BVD virus. An anti-BVD serum protein-horseradish peroxidase conjugate was prepared by coupling 0.5 ml of anti-BVD antiserum dialyzed against sodium carbonate buffer to 5 mg of horseradish peroxidase as in the previous Example. The resulting product was designated conjugate[3].

The standard antigen employed in the immunoassay originated from a commercial BVD vaccine, consisting of killed whole virus suspended in saline containing an unknown quantity of bovine serum albumin (added as a stabilizer) and a variety of anti-microbial agents. The quantity of viral antigen per unit volume of the vaccine was not disclosed by the manufacturer. The vaccine was dialyzed overnight at 4° C. against PBS prior to use.

Macroporous polypropylene filter cloth pieces were coated with 60 μl of partially denatured anti-BVD antiserum (i.e., heated at 75° C. for 10 minutes) and incubated at room temperature as previously described. Antibody-coated macroporous hydrophobic cloths were incubated for 30 minutes at room temperature with 30 μl of dialyzed BVD vaccine diluted either 1 10, 1:100 or 1:1,000 in PBS. Undiluted vaccine and PBS alone were also included in the series, and each macroporous hydrophobic cloth was prepared in quadruplicate. After the incubation period, the macroporous hydrophobic cloths were washed with PBST and probed with 25 μl of conjugate[3] diluted 1:100 in PBST, as previously. These were than assayed by immersion in 0.5 ml of ABTS-indicator solution for 30 minutes. The results are shown below in Table 5.

TABLE 5

Detection of BVD Antigen by the Enzyme Immunoassay

| Antigen Dilution | $A_{650}$ | | | |
|---|---|---|---|---|
| | 1 | 2 | 3 | 4 |
| undiluted | 1.230 | 1.190 | 1.090 | 1.200 |
| 1:10 | 0.246 | 0.280 | 0.265 | 0.210 |
| 1:100 | 0.091 | 0.110 | 0.115 | 0.095 |
| 1:1000 | 0.060 | 0.071 | 0.055 | 0.050 |
| no antigen | 0.055 | 0.053 | 0.051 | 0.042 |

Table 5 shows that the detectability of the BVD assay, in the form tested, was fixed somewhere in the range of 1:10 to 1:100 dilution of the dialyzed vaccine. These results clearly demonstrate the ability of the immunoassay to detect BVD antigen.

II(c) Alternative Solid Phases for Use in the Enzyme Immunoassay

A series of Examples was carried out to determine the usefulness of other materials as solid phases for capture and detection of *B. abortus* cells.

Macroporous polypropylene filter cloth was compared to a variety of other materials employed as solid phases in the immunoassay. The materials tested were macroporous 100% nylon cloth (acquired locally), in the Ottawa, Canada area, macroporous woven polyester cloth (acquired locally), in the Ottawa, Canada areas, macroporous nonwoven polyester cloth (DuPont), cellulose acetate membrane (Gelman), cellulose nitrate membrane (Schleicher and Schuell), analytical paper (Schleicher and Schuell), and a macroporous polyethylene filter (1.5 mm thickness, supplier unknown). These were all cut into 6×6 mm square pieces, and coated with 60 μl of partially denatured bovine anti-Brucella antiserum diluted 1:10 in PBS, as previously. The materials were then incubated with 30 μl of *B. abortus* cells diluted to $4 \times 10^7$ cells/ml in PBS for 30 minutes at room temperature. A parallel series to which PBS containing no antigen was added was also included, and each solid phase was prepared in duplicate. After the incubation period, the materials were washed with PBST and probed with conjugate (prepared with affinity purified antibody) as usual. These were then assayed by immersion in 0.5 ml of ABTS-indicator solution for 30 minutes. The performance of each solid phase in the assay is shown below in Table 6.

TABLE 6
Performances of Various Solid Phases Employed in the Enzyme Immunoassay

| | $A_{650}$ | | | |
|---|---|---|---|---|
| | specific[a] | | control[b] | |
| Solid Phase | 1 | 2 | 1 | 2 |
| Polypropylene filter cloth | 0.428 | 0.430 | 0.012 | 0.010 |
| Nylon cloth | 0.320 | 0.338 | 0.011 | 0.009 |
| Woven polyester cloth | 0.840 | 0.860 | 0.035 | 0.026 |
| Nonwoven polyester cloth[c] | 0.810 | 0.792 | 0.033 | 0.020 |
| Cellulose acetate membrane | 0.220 | 0.186 | 0.100 | 0.122 |
| Cellulose nitrate membrane | 0.282 | 0.235 | 0.185 | 0.192 |
| Polyethylene filter | 0.450 | 0.455 | 0.061 | 0.072 |
| Analytical paper | 0.416 | 0.422 | 0.400 | 0.421 |

[a]Cloths incubated with antigen
[b]Cloths incubated without antigen
[c]A variety of DuPont polyester cloths were examined and the results with these cloths were similar to data shown here Table 6 shows that of the solid phases tested, the highest signals were obtained with the macroporous woven polyester and macroporous nonwoven polyester cloths. Other materials that are useful in the enzyme immunoassay are macroporous nylon cloth and the macroporous polyethylene filter, which produce similar results to those obtained using macroporous polypropylene filter cloth.

The main advantage of macroporous hydrophobic cloths as supports in enzyme immunoassay is that they provide a large volume for absorption per surface area for antigen-antibody interaction. Macroporous polyethylene, macroporous nylon, and macroporous polyester cloths, by virtue of their hydrophobic characteristics, have been found to adsorb and absorb antibodies and thus provided a large surface area for antigen capture. Other materials amenable to the enzyme immunoassay concept should have included cellulose acetate and cellulose nitrate membranes and filter paper. However as the results above indicated, they are not useful according to the present invention.

IV Comparison of the Enzyme Immunoassay Using Macroporous Polypropylene Filter Cloth, a Flat Polypropylene Sheet and a Polystyrene Microtiter Plate Surface The enzyme immunoassay response arising from the use of an antibody-coated plastic polypropylene sheet and a polystyrene microtiter surface, which have very limited surface areas available for antibody adsorption, and hence antigen capture, to the assay response obtained using macroporous hydrophobic polypropylene filter cloth when various quantities of antigen are applied was compared.

A flat polypropylene sheet, cut into 6×6 mm pieces, was coated with anti-Brucella antibodies as were 6×6 mm pieces of polypropylene filter cloth. Several wells in a polystyrene microtiter plate were also coated. These were then incubated with 30 µl of PBS containing either $1.2 \times 10^7$, $1.2 \times 10^6$, $1.2 \times 10^5$, $1.2 \times 10^4$, B. abortus cells (plate test antigen), or PBS alone, for 30 minutes at room temperature. The materials were subsequently processed in the enzyme immunoassay as in the previous Example, with the exception that enzyme activity was assayed by immersion in 0.5 ml of ABTS-indicator solution for 3 hours. Each determination was done in triplicate, and the results are shown below in Table 7.

TABLE 7
Detectability of the Enzyme Immunassay Employing Three Different Solid Phases.

| | No. of Cells Applied Per Piece | | | | |
|---|---|---|---|---|---|
| $A_{650}$ | $1.2 \times 10^7$ | $1.2 \times 10^6$ | $1.2 \times 10^5$ | $1.2 \times 10^4$ | 0 |
| Polypropylene 1 | 5.02 | 1.02 | 0.29 | 0.09 | 0.04 |
| Filter 2 | 5.12 | 1.24 | 0.29 | 0.08 | 0.03 |
| Cloth 3 | 5.30 | 1.15 | 0.24 | 0.08 | 0.03 |
| Plastic 1 | 1.02 | 0.43 | 0.06 | 0.03 | 0.04 |
| Polypropylene 2 | 1.01 | 0.32 | 0.07 | 0.02 | 0.04 |
| Sheet 3 | 0.96 | 0.87 | 0.07 | 0.04 | 0.03 |
| Polystyrene 1 | 1.08 | 0.28 | 0.08 | 0.02 | 0.03 |
| Microtiter Plate 2 | 1.22 | 0.35 | 0.09 | 0.03 | 0.04 |
| Surface 3 | 1.01 | 0.30 | 0.08 | 0.04 | 0.02 |

Table 7 shows that the successful detection of very small quantities of antigen must require a significantly large capturing surface in order to increase the probability of interaction between the solid phase and the antigen during the limited incubation period involved. This expectation is confirmed by the results obtained using an antibody-coated plastic polypropylene sheet and a polystyrene microtiter plate surface as solid phases, which failed to detect small quantities of antigen to which the macroporous hydrophobic polypropylene cloth responded, and which showed a greatly diminished sensitivity throughout the range of antigen concentration tested.

V Commercial Adaptation of the Enzyme Immunoassay: Dipstick of Hydrophobic Cloth A commercial form of the enzyme immunoassay was developed for application of the enzyme immunoassay in any number of circumstances (e.g., diagnostic laboratory and field testing, etc.). One practical form consists of affixing a small rectangular piece of macroporous polypropylene filter cloth to a strip, e.g. of cellulose acetate, which allows for the easy retrieval of the antibody-coated macroporous hydrophobic cloth from test samples and provides a convenient means of handling the macroporous hydrophobic cloth throughout the assay procedure. It is necessary to ensure that the bond created between the macroporous polypropylene cloth and the cellulose acetate does not alter the properties of the former or result in any structural features of the macroporous hydrophobic cloth/strip junction which might cause non-specific retention of the conjugate.

A bond was created by first dissolving one edge of a cellulose acetate strip having the dimensions 2½×¼ macroporous polypropylene cloth piece of the same thickness, making sure not to allow any overlapping of one edge over the other. Upon evaporation of the acetone, a strong bond was formed between the cellulose acetate strip and the macroporous polypropylene filter cloth piece. The cloth portion of the resulting test strip was coated with antibody by applying 100 µl of partially denatured bovine anti-Brucella antiserum diluted 1:10 in PBS and incubating overnight at room temperature, followed by washing with PBST as previously described. The antibody-coated test strip was tested in the enzyme immunoassay in the manner described below.

Test strips were incubated with either 30 µl of PBS containing $1.2 \times 10^6$ B. abortus cells (plate test antigen) or 30 µl of PBS alone, for 30 minutes at room temperature. These were then washed with PBST and incubated for 30 minutes at room temperature with 25 μl of conjugate[1] diluted 1:1,000 in PBST. The macroporous hydrophobic cloth portions of the test strips were then washed with PBST, and were subsequently assayed for retained enzyme activity by immersion in 1 ml ABTS-indicator solution for 30 minutes with gentle shaking. The reaction was stopped by addition of 0.5 ml of 0.1M NaF and absorbance was read at 650 nm. Each determination was performed in quadruplicate, and the results of the assay are shown below in Table 8.

TABLE 8

Application of Antibody-Coated Test Strips in Enzyme Immunoassay

| No. of Cells Applied per Test Strip | $A_{650}$ | | | |
|---|---|---|---|---|
| | 1 | 2 | 3 | 4 |
| $1.2 \times 10^6$ | 0.411 | 0.427 | 0.415 | 0.435 |
| 0 | 0.023 | 0.016 | 0.020 | 0.021 |

The results of the enzyme immunoassay demonstrate the ability of the antibody-coated test strips to detect *B. abortus* antigens at the concentration tested. The background level of enzyme activity was negligible, thus satisfying one of the important requirements of the immunoassay. These results were reproducible.

V Application of a Macroporous Hydrophobic Cloth as an Adsorbant and Absorbant of Antigen in Enzyme Immunoassay for *B. Abortus* LPS.

The following experiment shows the application of macroporous hydrophobic cloth as an adsorbent and absorbent of antigen for the immunoassay.

Macroporous polyester non-woven cloths (DuPont SONTARA 8100™) were incubated with 50 μl per 6×6 mm piece of 2 μg/ml solution of *B. abortus* LPS in PBS, overnight at room temperature.

The macroporous hydrophobic cloths were then washed with PBST. Each cloth was incubated for 30 min., at room temperature, with 25 μl of either of the following preparations: 50 μl of PBS containing 90 ng of *B. abortus* LPS plus 25 μl of antibody-horseradish peroxidase conjugate diluted 10,000× in PBST, 50 μl of PBS containing a ng of 1PS plus 25 μl of diluted conjugate, 50 μl of PBS containing 0.9 ng of LPS plus 25 μl of diluted conjugate, or 50 μl of PBS alone plus 25 μl of diluted conjugate.

The macroporous hydrophobic cloths were then washed with PBST and assayed for HRP by immersion in 0.5 ml of ABTS-indicator for 90 min., at room temperature. The reaction was stopped by addition of 0.5 ml of 0.1M NaF, and absorbance were read at 650 nm. The results of this experiment are recorded in Table 9 below.

TABLE 9

Enzyme Immunoassay for the Detection of *B. Abortus* LPS Using Macroporous Polyester Non-Woven Cloths

| LPS (ng) applied per cloth | $A_{650}$ 1 | 2 | Visual observation |
|---|---|---|---|
| 30 | 0.02 | 0.01 | yes |
| 3 | 0.127 | 0.115 | yes |
| 0.3 | 0.22 | 0.20 | no |
| 0 | 0.20 | 0.23 | — |

The results show clearly that at least 30 ng and 3 ng of LPS were detectable by simple visual examination, where the corresponding samples produced less colour than the control. However, it is equally important to note that the enzyme immunoassay might successfully detect even lower quantities of LPS by colorimetric measurement. The enzyme immunoassay offers the distinct advantages of providing an internal control for conjugate quality and requiring only one incubation step for the decisive immunological reaction. Such advantages make the enzyme immunoassay more easily adaptable for field testing.

It is believed that the detectability limit of this enzyme immunoassay may be improved by coating the macroporous polyester cloth with a limited quantity of antigen, making the free antigen present in the test sample more competitive for the conjugate.

An improved enzyme-antibody conjugate having a higher specific activity has also been provided which should allow for the use of highly diluted conjugate in the assay, thus describing the quantity of free antigen required to prevent attachment of the conjugate to the macroporous hydrophobic cloth (thus increasing the sensitivity of antigen detection).

GENERAL OBSERVATIONS

The enzyme immunoassay device of this invention thus employs macroporous hydrophobic cloths as surfaces. Macroporous hydrophobic fabrics (cloths) of plastics, e.g. polypropylene and polyester, are moderately priced because of their large commercial demand as textiles and filters. These cloths offer the following advantages over the previous adsorption supports: they can accommodate a larger volume of sample per area; have a larger surface area for binding immunoreactants and for immunoreactions; are easily washed because of minimum flow resistance; and have both strength and durability.

The enzyme immunoassay procedure for detecting antigens in test samples using antibody-coated macroporous hydrophobic cloths was found to be fast and simple, requiring only the most basic instruments found in most research and clinical laboratories. The enzyme immunoassay is also designed so that a qualitative result can be obtained in field test situations, where access to instrumentation is limited or non-existant.

The enzyme immunoassay procedure is a rapid and simple procedure which can be applied for the direct detection of antigens in test samples. The assay can be easily and economically adapted for field testing, where a positive result could easily be distinguished from a negative one by visual assessment of the substrate-indicator, (e.g. ABTS), which produces a blue-green colour in the presence of horseradish peroxidase. The "dipstick" format of the field kit makes the manipulation of antibody-coated macroporous hydrophobic cloth throughout the procedure simple and convenient, so that the test can be performed by untrained hands. Furthermore, this format obviates the need for even common laboratory equipment, and all necessary reagents can be easily supplied in the form of a kit.

Although horseradish peroxidase was used as an indicator, any other suitable enzyme, e.g. alkaline phosphatase and β-galactosidase, can be employed in the enzyme-antibody conjugate for the detection of antigens. Also, monovalent antigens e.g. toxins (i.e., haptens) can be detected by the second embodiment of the enzyme immunoassay method. In this second embodiment of the enzyme immunoassay, a standard preparation of the monovalent antigen could be immobilized on the macroporous hydrophobic cloth surface by adsorption or via a hydrophobic carrier. A test sample suspected of harboring the antigen would then be mixed with an enzyme-antibody conjugate specific for that antigen and incubated with the antigen-coated macroporous hydrophobic cloth. A negative control in which a representative sample devoid of antigen is mixed with the conjugate would be incubated with a separate antigen-coated macroporous hydrophobic cloth. Since the presence of free antigen in the test sample should prevent binding of the conjugate to the macroporous hydrophobic cloth surface, the enzyme immunoassay result would be obtained by comparing the amount of enzyme immobilized on the test macroporous cloth with that obtained on the negative control macroporous hydrophobic cloth. Thus, the enzyme immunoassay is amenable to a variety of assay forms, the exact form being determined by the nature of the specific antigen being detected.

The results obtained indicate that several types of macroporous hydrophobic cloths can be used as solid phases for the adsorption of antibodies. These include macroporous polypropylene macroporous polyester, macroporous nylon, and macroporous polyethylene cloths, all of which were found to be suitable adsorbents for antibody, e.g. anti-Brucella antibody. All those macroporous hydrophobic cloths have proven successful for the detection of antigens such as *B. abortus* antigens.

It has been found that whole bovine antiserum containing antibody with the appropriate antigen-specificity can be used to coat macroporous hydrophobic cloth when heated at 75° C. for 10 minutes. This obviates the need for purified antibody preparations, which are time-consuming to produce and may entail some expense. However, in order to minimize the potential for cross-reactions it is preferred that enzyme-antibody conjugates be prepared using purified antibodies. Since the conjugate can be diluted up to 1,000 times, only a small amount of conjugate stock need be prepared in this manner, thus maintaining the ease and economy of each individual test.

The detection of *Brucella abortus* (the causative agent of bovine brucellosis) was used to test the utility of the method of this invention. Using the macroporous hydrophobic cloth carriers of this invention coated with whole antiserum preheated at 75° C. for 10 minutes, the enzyme immunoassay was able to detect 0.3 nanograms of *B. abortus* lipopolysaccharide and $10^4$ *B. abortus* whole cells. The macroporous polypropylene cloth-based enzyme immunoassay was also successfully adapted for the detection of bovine viral diarrhea (BVD) antigen.

As noted above *Brucella abortus* was used to examine the performance of macroporous hydrophobic cloth as adsorbents of immunoreactants. *B. abortus* causes brucellosis, a serious disease of humans and cattle. Confirmation of the brucellosis by the cultural diagnosis is a slow, complicated process of uncertain sensitivity. Rapid, simple and sensitive detection of Brucella antigens will facilitate confirmation and thus surveillance of brucellosis and its control.

Macroporous polypropylene cloth has been found to have excellent properties as a solid phase in the enzyme immunoassay. The fact that macroporous polypropylene filter cloth is available in a nonwoven filter cloth form gives it the added advantage of retaining a stable fabric structure (i.e., no loose edges) even under agitated conditions. Furthermore, macroporous polypropylene filter cloth is easily adapted for the preparation of commercial test kits.

The detection of *B. abortus* antigens by antibody-coated macroporous hydrophobic cloths is only one example of the method of this invention for the study of microbial antigen detection by cloth enzyme immunoassay. The enzyme immunoassay method is amenable to the detection of any given number of microbial antigens, provided that these are sufficiently small to be retained on the antibody-coated macroporous hydrophobic cloths throughout the enzyme immunoassay procedure. In cases where antigens, e.g. whole cells, are too large for effective retention on the macroporous hydrophobic cloths, important antigenic components thereof might be dissociated from the surface by simple chemical or mechanical means so as to facilitate detection.

For example, the present invention is applicable to many immunologically reactive materials, e.g. proteins, peptides, polysaccharides, etc. which are of decisive significance for an immunological determination, i.e. the presence of these materials is the determining factor in the immunological test procedure. These materials can be detected in the body fluids of humans and animals using immunological principles or can serve for their detection. Especially suitable immunologically-reactive materials are pathogenic and vacultatively pathogenic organisms such as, for example, parasites, protozoa, bacteria or viruses or their immunologically active components, isolated antibodies from humans and animals, serum constituents, toxins, hormones, enzymes, alkaloids, cell and tissue extracts, substances with a small molecular weight such as, for example, insulin, anngiotensin and urokinase, biogenic amines, blood cells, particles chemically or physically covered with antigens or antibodies, such as, for example, erythrocytes or latex particles.

The following Table provides a selection of typical diseases or conditions which can be determined with the aid of the immunoassay device in accordance with the present invention according to the immunologically reactive materials lyophilised thereon.

TABLE

| Antigen | Disease |
| --- | --- |
| Toxoplasma gondii | Toxoplasmosis |
| Entamoeba histolytica | Amoebiasis |
| Trypanosoma cruzi | Chagas |
| Trypanosoma gambiense/rhodesiense | Sleeping sickness |
| Leishmania donovani | Leishmaniasis |
| Schistosoma mansoni | Schistosomiasis |
| Echinococcus granulosus | Echinococcosis |
| Filariae | Filariasis |
| Fasciola hepatica | Fascioliasis |
| Plasmodia | Malaria |
| Candida species | Candidiasis |
| Aspergilli | Asperigillosis |
| Mycropolyspora faeni/Micromonospora vulgaris | Farmer's lung |
| Treponema pallidum | Syphilis |
| Neisseria gonorrhoeae | Gonorrhea |
| Neissseria meningitis | Meningitis |
| Brucella abortus | Brucellosis |
| Mycoplasma pneumoniae | Pneumonia |
| Australia antigen | Acute hepatitis |
| Herpes simplex virus | Herpes simplex |
| Influenza virus | Flu |
| Cell nuclei | Systemic *lupus erythrematosis* or Scleroderma |
| Cryptococci | Cryptococcosis |
| Torulopsis species | Systemic mycosis |
| H-antigen | Salmonella |

| Antigen | Disease |
|---|---|
| (flagellar) | |

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What we claim is:

1. An enzyme immunoassay device comprising the combination of (a) a macroporous hydrophobic synthetic polymer woven or non-woven cloth having a thickness of more than about 200 μm and having spaces between fibres exceeding about 20 μm in diameter, the cloth consisting entirely of unmodified hydrophobic threads formed of a synthetic polymer selected from the group consisting of polypropylene, polyester, nylon, and polyethylene; and (b) an unmodified antibody or an unmodified antigen directly adsorbed thereon and directly absorbed therein; the cloth having a Frazier Air Permeability in CFM/ft$^2$ at 0.5"H$_2$O of about 215 for a cloth of thickness about 40 mils, the cloth thereby having such porosity that it can accommodate a large volume of per surface area thereof, that it has a large surface area for binding to the antibody or the antigen, respectively, and that it has minimum flow resistance.

2. The enzyme immunoassay device of claim 1 wherein said antibody is provided by an antiserum containing an antibody specific for the antigen being tested.

3. The enzyme immunoassay device of claim 2 wherein said antibody present in said antiserum have been partially denatured, by exposure to a low pH environment or by heating.

4. The enzyme immunoassay device of claim 3 wherein said partial denaturization is achieved.

5. The enzyme immunoassay device of claim 4 wherein said antibodies present in said antiserum have been affinity-purified.

6. The enzyme immunoassay device of claim 1 wherein said antibody is provided by a purified antibody bearing the appropriate specificity, which is either diluted or undiluted.

7. The enzyme immunoassay device of claim 1 in the form of said macroporous hydrophobic synthetic polymer cloth which is bonded to a different material, thereby to provide an antibody-coated test strip that may be handled throughout an enzyme assay procedure.

8. An enzyme immunoassay method for detecting an antigen comprising the steps of: a) treating a surface of an immunoassay device comprising a macroporous hydrophobic synthetic polymer woven or non-woven cloth having a thickness of more than about 200 μm and having spaces between fibres exceeding about 20 μm in diameter, said cloth consisting entirely of unmodified hydrophobic threads formed of a synthetic polymer selected from said group consisting of polypropylene, polyester, nylon, and polyethylene with an unmodified antibody, thereby to have an antibody directly adsorbed thereon and directly absorbed therein, said cloth having a Frazier Air Permeability in CFM/ft$^2$ at 0.5"H$_2$O of about 215 for a cloth of thickness about 40 mils, said cloth thereby having such porosity that it can accommodate a large volume of liquid per surface area thereof, that it has a large surface area for binding to said antibody and that it has minimum flow resistance, thereby to provide an antibody surface-treated cloth; b) applying, to said surface of said antibody surface-treated cloth, an antigen being assayed, thereby to provide an antigen-treated cloth; (c) incubating said antigen-treated cloth with a sample to be tested for said antigen, thereby to provide an incubated cloth; d) washing said incubated cloth with a buffer to remove unadsorbed material, thereby to provide a washed cloth; e) incubating said washed cloth with an enzyme-antibody conjugate prepared by coupling purified antibody specific for said antigen to a suitable indicator enzyme, thereby to provide an incubated washed cloth; f) washing said incubated washed cloth with a buffer to remove unreacted conjugate; and g) detecting enzyme-antibody conjugate remaining thereon by incubation in a chromogenic substrate indicator solution to produce a visible colour upon product formation, indicative of said presence of an antigen 9. An enzyme immunoassay method for detecting an antibody comprising the steps of: a) treating a surface of an immunoassay device comprising a macroporous hydrophobic synthetic polymer woven or non-woven cloth having a thickness of more than about 200 μm and having spaces between fibres exceeding about 20 μm in diameter, said cloth consisting entirely of unmodified hydrophobic threads formed of a synthetic polymer selected from said group consisting of polypropylene, polyester, nylon, and polyethylene with an unmodified antigen, thereby to have an antigen directly adsorbed thereon and directly absorbed therein, said cloth having a Frazier Air Permeability in CFM/ft$^2$ at 0.5"H$_2$O of about 215 for a cloth of thickness about 40 mils, said cloth thereby having such porosity that it can accommodate a large volume of liquid per surface area thereof, that it has a large surface area for binding to said antigen and that it has minimum flow resistance; thereby to provide an antigen surface-treated cloth; b) applying, to said surface of said antigen surface-treated cloth, an antibody being assayed, thereby to provide an antibody-treated cloth; c) incubating said antibody-treated cloth with a sample to be tested for said antibody, thereby to provide an incubated cloth; d) washing said incubated cloth with a buffer to remove unadsorbed material, thereby to provide a washed cloth; e) incubating said washed cloth with an enzyme-antibody conjugate prepared by coupling purified antibody specific for the test antibody to a suitable indicator enzyme, thereby to provide an incubated washed cloth; f) washing said incubated washed cloth with a buffer to remove unreacted conjugate; and g) detecting enzyme-antibody conjugate remaining thereon by incubation in a chromogenic substrate indicator solution to produce a visible colour upon product formation, indicative of said presence of an antibody.

10. An enzyme immunoassay method for detecting an antibody comprising the steps of: a) treating an immunoassay device comprising a macroporous hydrophobic synthetic polymer woven or non-woven cloth having a thickness of more than about 200 μm and having spaced between fibres exceeding about 20 μm in diameter, said cloth consisting entirely of unmodified hydrophobic threads formed of a synthetic polymer selected from said group consisting of polypropylene, polyester, nylon, and polyethylene with an unmodified antibody, thereby to have an antibody directly adsorbed thereon and directly absorbed therein, said cloth having a Frazier Air Permeability in CFM/ft$^2$ at 0.5"H$_2$O of about 215 for a cloth of thickness about 40 mils, said cloth thereby having such porosity that it can accommodate a large volume of liquid per surface area thereof, that it has a large surface area for binding to said antibody and that it has minimum flow resistance, thereby to provide an antibody surface-treated cloth; b) applying to said surface of said antibody surface-treated cloth, a mixture of said antibody being assayed and an enzyme-antigen conjugate specific for said antibody adsorbed onto said cloth, thereby to provide an antibody/enzyme-antigen conjugate treated cloth; c) applying, to a surface of a control cloth identical to said hydrophobic synthetic polymer cloth, said same enzyme-antigen conjugate, thereby to provide an enzyme-antigen conjugate treated control cloth; d) incubating both said antibody/enzyme-antibody conjugate treated cloth and said enzyme-antigen conjugate treated control cloth substantially simultaneously, to provide incubated cloths; e) washing both said incubated antibody/enzyme-antigen conjugate treated cloth and said incubated enzyme-antigen conjugate treated control cloth with a buffer solution; and f) detecting said antibody by incubation of both said washed antibody/enzyme-antigen conjugate treated cloth and said washed enzyme-antigen conjugate treated control cloth in a chromogenic substrate indicator solution to produce a visible colour upon product formation indicative of said presence of antibody, the amount of said antibody being determined by the difference in intensity of said colour on said antibody/enzyme-antigen conjugate treated cloth and said colour on said enzyme-antigen conjugate treated control cloth.

11. An enzyme immunoassay method for detecting an antigen comprising the steps of: a) treating an immunoassay device comprising a macroporous hydrophobic synthetic polymer woven or non-woven cloth having a thickness of more than about 200 µm and having spaced between fibres exceeding about 20 µm in diameter, said cloth consisting entirely of unmodified hydrophobic threads formed of a synthetic polymer selected from said group consisting of polypropylene, polyester, nylon, and polyethylene with an unmodified antigen, thereby to have an antigen directly adsorbed thereon and directly absorbed therein, said cloth having a Frazier Air Permeability in CFM/ft$^2$ at 0.5"H$_2$O of about 215 for a cloth of thickness about 40 mils, said cloth thereby having such porosity that it can accommodate a large volume of liquid per surface area thereof, that it has a large surface area for binding to said antigen and that it has minimum flow resistance, thereby to provide an antigen surface-treated cloth; b) applying to said surface of said antigen surface-treated cloth a mixture of said antigen being assayed and an enzyme-antibody conjugate specific for said antigen adsorbed onto said cloth, thereby to provide an antigen/enzyme-antibody conjugate treated cloth; c) applying, to a surface of a control cloth identical to said hydrophobic synthetic polymer cloth, the same enzyme-antibody conjugate, thereby to provide an enzyme-antibody conjugate treated control cloth; d) incubating both said antigen/enzyme-antibody conjugate treated cloth and said enzyme-antibody conjugate treated control cloth substantially simultaneously to provide incubated cloths; e) washing both said incubated antigen/enzyme-antibody conjugate treated cloth and said incubated enzyme-antibody conjugate treated control cloth with a buffer solution; and f) detecting said antigen by incubation of both said antigen/enzyme -antibody conjugate treated cloth and said enzyme-antibody conjugate treated control cloth in a chromogenic substrate indicator solution to produce a visible colour upon product formation, indicative of the presence of said antigen, the amount of said antigen being determined by the difference in intensity of the colour on said antigen/enzyme-antibody conjugate treated cloth and the colour on said enzyme-antibody conjugate treated control cloth.

* * * * *